United States Patent [19]

Okazaki

[11] Patent Number: 4,689,670
[45] Date of Patent: Aug. 25, 1987

[54] METHOD AND APPARATUS FOR MEASURING A BIOLOGICAL FUNCTION OF A SUBJECT

[75] Inventor: Kiyoshi Okazaki, Takanezawa, Japan

[73] Assignee: Kabushiki Kaisha Toshiba, Kawasaki, Japan

[21] Appl. No.: 693,168

[22] Filed: Jan. 22, 1985

[30] Foreign Application Priority Data

Jan. 19, 1984 [JP] Japan ................................ 59-6266

[51] Int. Cl.$^4$ .............................................. H04N 5/32
[52] U.S. Cl. ........................................ 358/111; 378/8; 378/95; 378/99
[58] Field of Search ................ 378/99, 8, 901, 98, 378/95; 358/111

[56] References Cited

U.S. PATENT DOCUMENTS 4,204,225  5/1980  Mistretta .
4,433,428  2/1984  Haendle et al. ..................... 378/8

OTHER PUBLICATIONS

Maeda et al., "A New Cardiac Functional Imaging by Application of Fourier Analysis to Gated Blood-Pool Study. A Basic Investigation", *Kakuigaku*, 19th, No. 5, pp. 765–776.

R. Brennacke et al., "Digital Processing of Videoangio-Cardiographic Image Series Using a Minicomputer", IEEE Cat. No. 76CH1160-1C, 1976, pp. 255–260.

"Patterns of Ventricular Emptying by Fourier Analysis of Gated Blood-Pool Studies", Jonathan M. Links et al., The Journal of Nuclear Medicine, pp. 978–982, vol. 21, 1980.

*Primary Examiner*—Janice A. Howell
*Attorney, Agent, or Firm*—Oblon, Fisher, Spivak, McClelland & Maier

[57] ABSTRACT

A method and apparatus for examining a subject by applying radiation to the subject in synchronism with a cardiac beat phase of the subject, wherein a digital subtraction is carried out between a mask image and a contrast image derived from the detected radiation which passed through the subject. Cardiac beat phase is detected by measuring the time-elapse characteristic data of image concentration. Based on the measuring time-elapse characteristic data, amplitude and phase images of the cardiac are calculated and displayed.

17 Claims, 10 Drawing Figures

METHOD AND APPARATUS FOR MEASURING A BIOLOGICAL FUNCTION OF A SUBJECT

BACKGROUND OF THE INVENTION

1. Field of the Invention

The present invention relates to a method and apparatus for measuring a biological function of a subject, e.g., a cardiac amplitude image and/or a cardiac phase image of the subject, using radiation, and more particularly to such a method and apparatus employing digital image processing.

2. Description of the Prior Art

A conventional radiation diagnostic apparatus, e.g., an X-ray diagnostic apparatus for obtaining X-ray images of circulatory organs by using an X-ray contrast medium, is disclosed as in U.S. Pat. No. 4,204,225 and U.S. Pat. No. 4,204,226 to Mistretta issued on May 20, 1980.

In an apparatus of this type, a digitally subtracted image is obtained between a mask image, i.e., an X-ray image taken before injection of an X-ray contrast medium to the circulatory organs, and a contrast image, i.e., an X-ray image taken after injection, so as to diagnose a region of interest in the circulatory organs.

However, in such an apparatus, it is very difficult to evaluate the biological cardiac function, i.e., cardiac amplitude and cardiac phase, etc., as the cardiac movement. It is impossible to evaluate the biological function quantitatively because, in the above conventional apparatus, an operator only observes the successive cardiac movement images on a monitor.

Furthermore, in a conventional apparatus, digital arithmetic operations such as addition or subtraction of the acquired images taken before and after injection of the X-ray contrast medium are performed on these images without taking account of natural pulsations of the circulatory organs. For this reason, undesirable artifacts occur due to differences among the cardiac beat phases in the diagnostic images. In addition, since an improvement of the concentration resolution is performed by adding images of different cardiac beat phases, the spatial resolution of these added images becomes low. Therefore, evaluating the biological function is hampered.

In the field of the nuclear medicine diagnosis, the journal titled "Kakuigaku" (produced by Hisato Maeda et al), the 19th, No. 5, pages 765–776, discloses a software method for obtaining the cardiac amplitude image and the cardiac phase image as a nuclear medicine image (i.e., a radioisotrope distribution image) using Fourier function development.

However, in the collection and preprocessing of images there is a difference between a digital fluoroscopy and the nuclear medicine.

SUMMARY OF THE INVENTION

Accordingly, an object of the present invention is to provide a novel radiation diagnostic method and apparatus for producing sharpened images without artifact due to differences in the cardiac beat phases.

Another object of this invention is to provide a novel radiation diagnostic method and apparatus which can quantitatively produce a diagnostic image including biological function information.

These and other objects are achieved according to the invention by providing a novel method for measuring a biological function of a subject and a novel apparatus for implementing the method, including means for obtaining a plurality of mask images in a complete cardiac period before an X-ray contrast medium arrives at a region of interest in the subject, means for obtaining a plurality of contrast images in another complete cardiac period after the X-ray contrast medium arrives at the region of interest; means for producing background removed imaged substantially affected by the contrast medium by subtracting the mask images from the contrast images in synchronism with cardiac phase; means for approximating a time-change of the background removed images into at least a first Fourier component image of the Fourier series thereof; and means for calculating at least one image of amplitude and phase of the first Fourier component image.

The method and apparatus according to the present invention can produce the amplitude image and the phase image of the cardiac beat movement from the X-ray penetration images during at least one cardiac beat period before and after the injection of the contrast medium, and these images can be displayed on the monitor quickly, whereby biological function of the heart can be measured and diagnosed quantitatively.

Furthermore, the acquired images are subtracted by a time-filtering process based upon the cardiac beat period. Therefore the present invention can produce the amplitude image and the phase image of the heart with high precision and without the artifact due to cardiac pulsatory movement.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
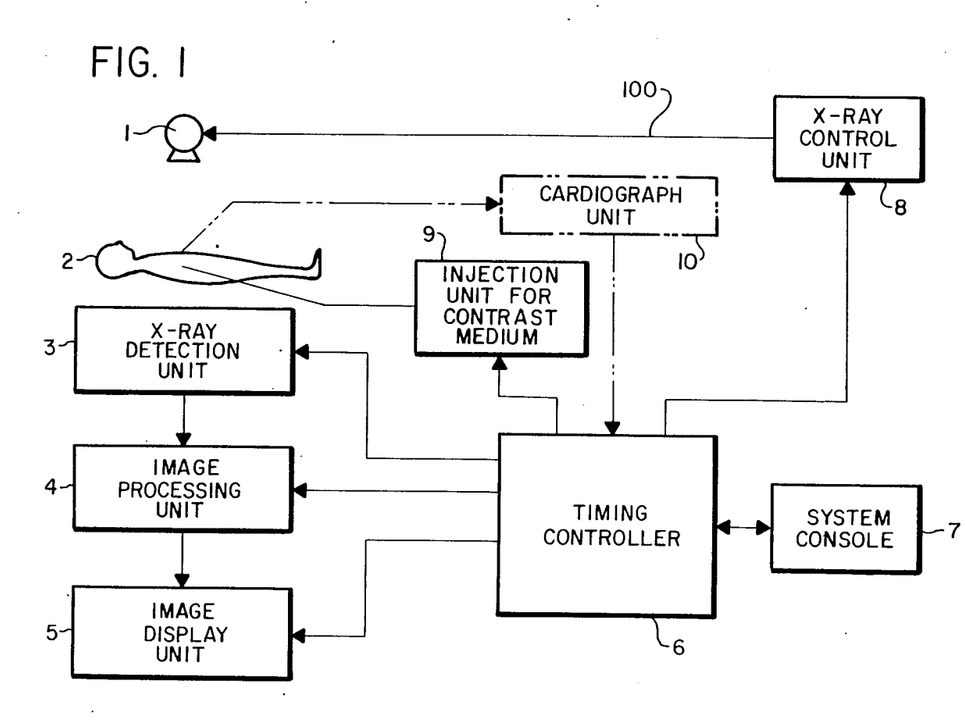
FIG. 1 is a schematic diagram of an X-ray diagnostic apparatus according to one preferred embodiment of the present invention.

Referring now to the drawings, wherein like reference numerals designate identical or corresponding parts throughout the several views, and more particularly to FIG. 1 thereof, which is a block diagram showing one embodiment of an X-ray diagnostic apparatus according to the present invention, an X-ray generator 1 projects X-ray radiation into a subject 2. An X-ray detection unit 3 is arranged opposite the X-ray generator 1 with the subject 2 therebetween. The X-ray detection unit 3 converts an X-ray transmission image into an analogue X-ray image signal. The X-ray detection unit 3 includes an image intensifier for the X-ray transmission image, an optical system for guiding an optical image provided from the image intensifier, a TV camera sensing the optical image guided by the optical system, and an A/D converter for converting an analogue signal provided from the TV camera into a digital signal. The optical image into which the image intensifier converts the X-ray transmission image is sensed by the TV camera to obtain a analogue signal representing the X-ray transmission image. The obtained analogue signal, i.e., a video signal, is converted into digital data by the A/D converter. The digital data is converted into a logarithmic value by a log converter.

An image processing unit 4 receives the digital data of the X-ray transmission image provided from the image detection unit 3, and stores the digital data for each frame of the television video. Images of the respective frames corresponding to a stored image taken before the injection of a contrast medium are digitally calculated so as to obtain an image representing a portion in which an image concentration changes in a predetermined region of interest. An image display unit 5 is connected to the image processing unit 4 so as to display the processed data provided from the image processing unit 4. The image display unit 5 includes a D/A converter (not shown in detail) for converting the digital data from the image processing unit 4 into analogue signals and a display for displaying the analogue signals.

Also provided is a timing controller 6, having a central processing unit (CPU), for controlling each unit.

A system console 7 having selection keys is provided for setting operation parameters, such as the exposure condition, the image processing mode and the control sequence, for example, with respect to a diagnostic portion of the subject 2. The operation parameters are previously programmed in the timing controller 6.

An X-ray control unit 8 is coupled to the timing controller 6 and controls the X-ray generator 1 so as to generate X-ray radiation in response to a control signal provided from the timing controller 6 according to operation parameters set by the system console 7.

An injection unit is provided for injecting a predetermined amount of the X-ray contrast medium into a blood vessel of the subject 2 at a predetermined time under control of the timing controller 6.

The image processing unit 4 will be described in more detail hereinafter.

Figure 2:
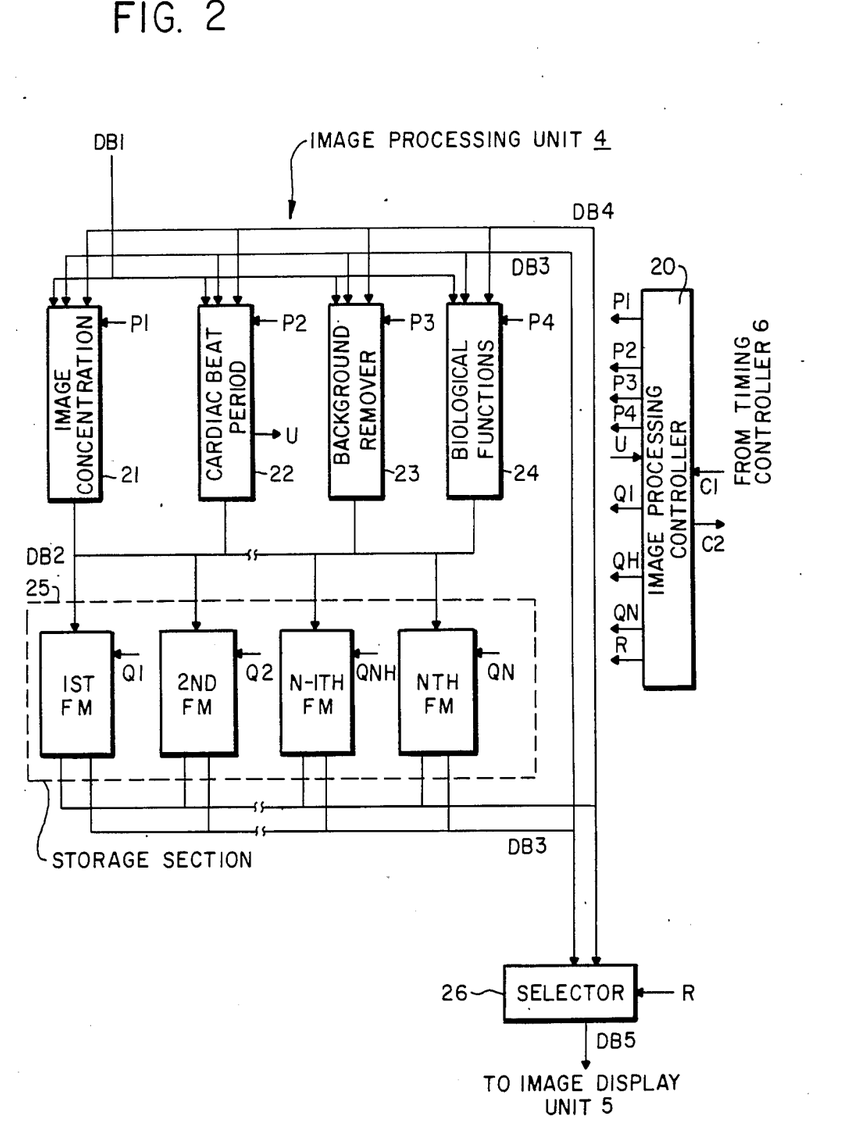
FIG. 2 is a block diagram of an internal circuit of the image processing unit 4 shown in FIG. 1.

As shown in FIG. 2, the image processing unit 4 includes an image processing controller 20, a device 21 for producing time-elapsed characteristic data of image concentration, a device 22 for detecting a cardiac beat period, a background removing device 23, a device 24 for measuring biological functions, an image storage section 25 for storing image data before and after processing, and a selector 26. The image processing controller 20 generated a control signal for controlling the sequential operation of the respective devices in the image processing unit 4 in response to a control signal C1 derived from the controller 6. The image processing controller 20 receives cardiac period and phase data of the subject 2 detected by the device 22 for detection of the cardiac beat period through a control line u. The image processing controller 20 supplies control signals to the background removing device 23, the device 24 for measuring biological functions, the image storage section 25, and the selector 26 through control lines p3, p4, Q1 to QN and R, respectively.

The device 21 for producing time-elapse characteristic data of image concentration receives image data provided from the X-ray detection unit 3 through a data bus DB1, image data provided from the image storage section 25 through a data bus DB3 and DB4, as described hereinafter, and measures time-changes of the image concentration averaged within a region of interest (ROI) i.e., a heart portion, determined by the timing controller 6, thus stores these time changes in one of the frame memories, and images of the ROI in other frame memories of the image storage section 25.

The device 22 for detecting cardiac beat period receives data on time-changes of image concentration obtained by the device 21 and stored in the frame memory so as to obtain a time instant representing maximal and minimal values of the image concentration from the time-elapse characteristic data, thereby detecting a period of cardiac beat and a change therein to detect the arrival of the contrast medium at the ROI. The device 22 then provides the relationships between the image numbers and the changes in the cardiac beat phases to the image processing controller 20 through the control line u.

The image storage section 25 includes N frame memories. A desired of the N frame memories is selected in response to frame output Q1 to QN from the image processing controller 20. A plurality of image data supplied through a data bus DB2 are sequentially stored at addresses in the selected frame memory by control of the image processing controller 20 and supplied onto the data buses DB3 and DB4. It should be noted that the data buses DB1, DB3 and DB4 are selected by a control signal from the processing controller 20.

Figure 3:
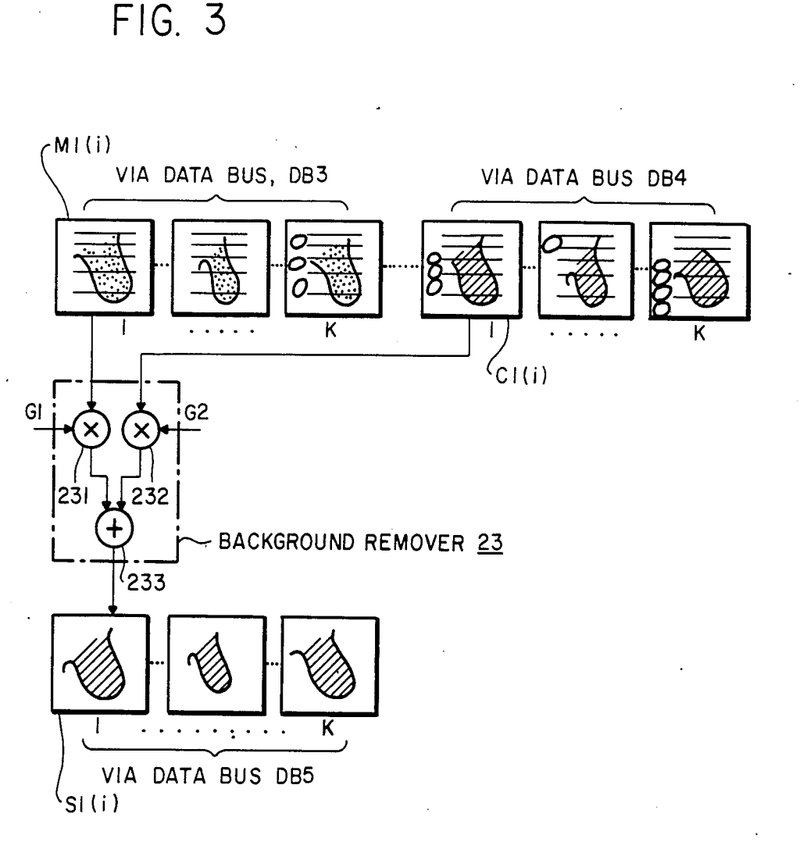
FIG. 3 is a functional block diagram of an internal circuit of the background removing device 23 shown in FIG. 2.

As shown in FIG. 3, the background removing device 23 includes multipliers 231 and 232 and an adder 233. The image processing controller 20 controls a multiplying operation of filter or weighting coefficients G1 and G2 in the multipliers 231 and 232 of the background removing device 23 through the control line p3. The multiplier 231 receives the mask image data before the contrast medium arrives at the ROI through the data bus DB3. It multiplies the mask image data by the weighting coefficient G1 and supplies the product to the adder 233. The multiplier 232 receives the contrast image data after the contrast medium arrives at the ROI and at the same phase of the mask image data, through the data bus DB4. It multiplies the contrast image data by the filter coefficient G2. The product is then supplied to the adder 233. The adder 233 adds these two products from two image data from the multiplier 231 and 232 so as to remove background which is not affected by contrast medium, and supplies the background removed image data SI(i) to the image storage section 25 through the data bus DB2.

Figure 4:
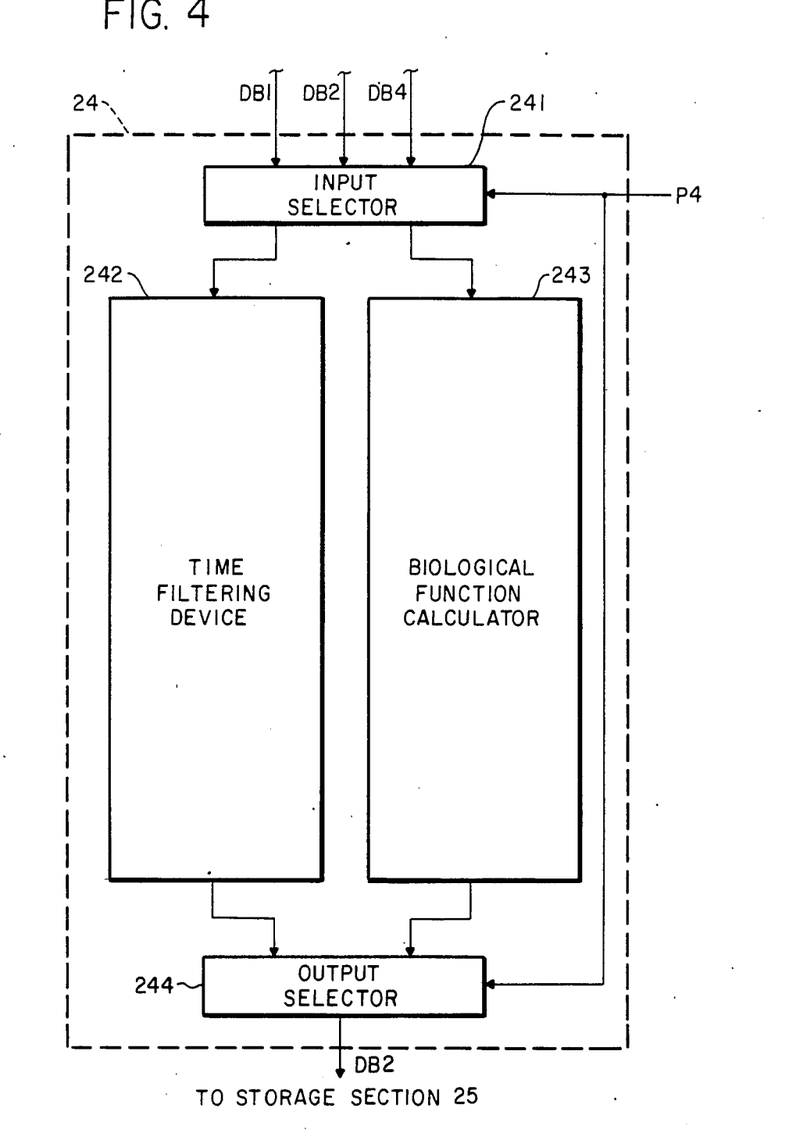
FIG. 4 is a block diagram of an internal circuit of the device 24 for producing biological function images.

As shown in FIG. 4, the device 24 for measuring biological functions includes an input selector 241, a time filtering device 242, a biological function calculator 243 and an output selector 244. The input selector 241 selects one of the data buses DB1, DB3 and DB4, and the selector 241 supplies data from the selected bus to either of the time filtering device 242 or the biological function calculator 243 in accordance with the control signal P4 from the image processing controller 20.

Figure 5:
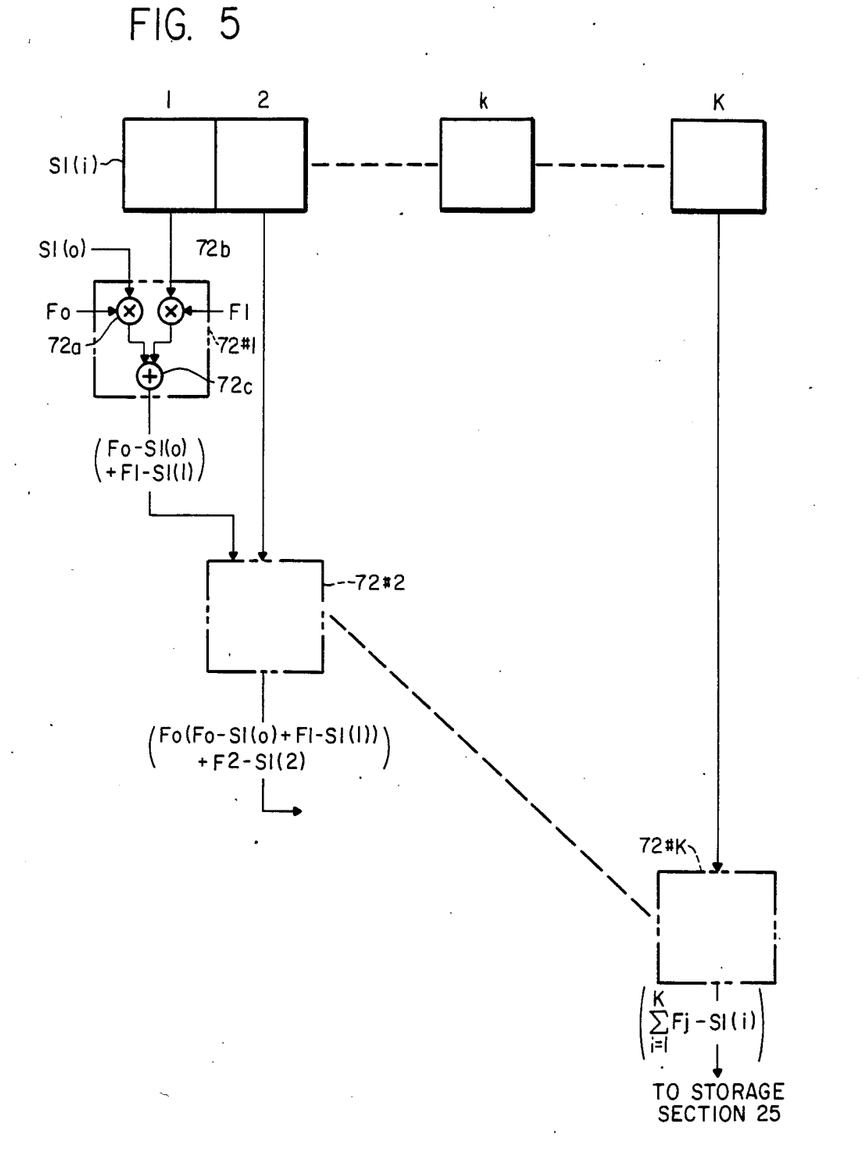
FIG. 5 is a block diagram illustrating operation of the time filtering device 242 provided within the biological function device 24 shown in FIG. 2.
Figure 6:
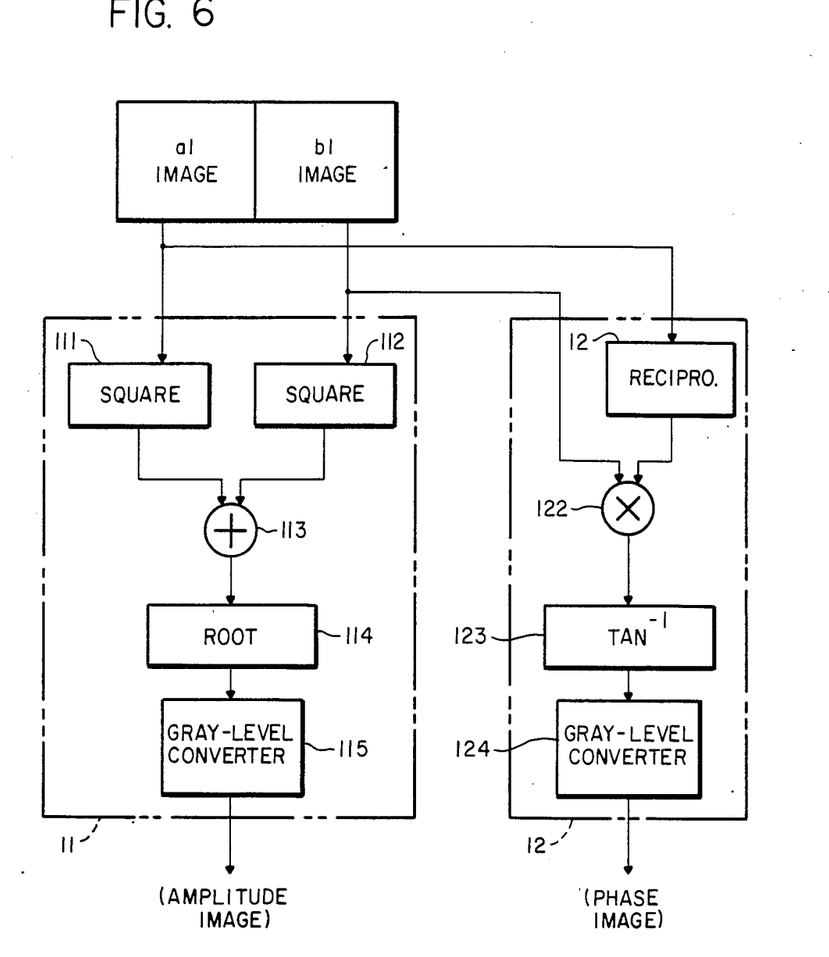
FIG. 6, is a block diagram of an amplitude imaging device 11 and a phase imaging device 12 provided within the biological function device 24 shown in FIG. 2.

The output selector 244 similarly selects one of the supplied outputs from either the device 242 or the calculator 243 in accordance with the control signal P4. The device 24 is controlled by the image processing controller 20 as as to receive the image data through the data bus DB1, DB3 and DB4. The device 24 includes the time filtering device 242 for calculating a coefficient of Fourier series as shown in FIG. 5, the cardiac amplitude imaging device 11 and the cardiac phase imaging device 12 as shown in FIG. 6 to measure biological functions. The devices 11 and 12 are controlled by the signals of the image processing controller 20.

The time filtering device 242 includes multiplier block 72#1 having multipliers 72a, 72b and adder 72c. The multiplier 72a is given the zero-cleared image data SI(0) through the data bus DB3 previously stored in the storage section 25. The background removed image data SI(1) of the first phase position are applied to the multiplier 72b through image data bus DB4. Then, weighting coefficients F0, F1 are multiplied to the respective image data applied to the multipliers 72a, 72b. Each of the multiplied image data is then supplied to the adder 72c for addition thereby.

The adder 72c calculates the image data of [F0 SI(0)+F1 (SI(1)]. The zero-cleared imge data SI(0) are all zero and F0 is 1. So the adder 72c produces the image data F1 Si(1). The image data F1 SI(1) is added to the next phase of image data SI(2) multiplied by coefficients F2 by the block 72#2. The block 72#2 produces the image data [F1 SI(1)+F2 SI(2)]. This operation is repeated over the complete cardiac period, i.e., until the image data SI(K), where K indicates the number of image frames collected in one cardiac beat period.

Thus the device produces the time filtered image given by the following equation (1):

$$TI = \sum_{j=1}^{K} Fj \cdot SI(j) \quad (1)$$

In equation (1), when the weighting coefficients (F) are defined by the following equation:

$$Fj=(2/K)\cdot\sin[2\pi C(j-1)/K].$$

image data "a1" are calculated. When the weight coefficients (Fj) are defined by the following equation;

$$Fj=(2/K)\cos[2\pi C(j-1)/K].$$

"b1" image data are calculated. Both a1 and b1 image data are temporarily stored in the section 25.

The cardiac amplitude imaging device 11, as shown in FIG. 6, includes two squaring device 111, 112, adder 113, square root calculation device 114 and gray-level converter 115. The a1 image data after application to the squaring device 111 through the image data bus DB3 from the image storage section 25 is squared by device 111. Similarly, the b1 image data applied to the squaring device 112 through the image data bus DB4 from the image storage section 25 is squared by device 112. Then, both the a1 and the b1 squared image data are added to each other by the adder 113. Thereafter, the square root of the added image data is calculated and is then converted to a gray-level by the gray-level converter 115. The output of converter 115 is amplitude image AI. The amplitude image AI is stored in the image storage section 25 via the image data bus DB2.

The cardiac phase image device 12, as shown in FIG. 6 includes a reciprocal device 121, multiplier 122, arc-tangent calculation device 123 and gray-level converter 124. The b1 image data is applied to the multiplier 122 via the image data bus DB3 from the image storage section 25, and the a1 image data is applied to the reciprocal device 121 via the image data bus DB4 from the image storage section 25. Therefore the a1 image data are converted into reciprocal image data (1/a1) and are applied to the multiplier 122.

The multiplier 122 multiplies the reciprocal image data (1/a1) by image data b1 and the arc-tangent of the product is calculated by the arc-tangent calculation device 123. The arc-tangent data are converted into a gray-leveled image (e.g., 256 gradients) by the gray-level converter 124. This image, designated as a phase image PI, is stored in the section 25 via the image data bus DB2.

The selector 26 shown in FIG. 2 includes a selection switch and selects one of the buses DB3 nd DB4 in response to a control signal R generated by the image processing controller 20. The selector 26 supplies the selected A1 and P1 image data to the image display unit 5 via the image data bus DB5.

Next described is the operation of the abovementioned embodiment.

First, the procedure of acquiring images taken before and after the injection of the X-ray contrast medium, i.e., mask and contrast images (MI(i), CI(i)), are described.

The system console 7 is provided with an image acquisition routine key (not shown in detail) to initiate acquisition of the images before and after the injection of the contrast medium. When the image acquisition routine key and a diagnosis region selection key also positioned in the system console 7, are operated, then the system controller 6 selects a predetermined image acquisition sequence, and X-ray projection conditions are applied to the X-ray control unit 8, thereby establishing parameters for projecting the X-ray. The controller 6 then sets the contrast medium injection unit 9 in the standby mode. Parameters are set so that the X-ray detection unit 3, the image processing unit 4 and the image display unit 5 operate in the standby mode.

When the image acquisition routine key is operated, the injection unit 9 is energized and the X-ray contrast medium is injected into the subject.

Next, under control of the X-ray control unit 8, X-ray radiation is irradiated and penetrates the subject before the contrast medium flows into the ROI. The X-ray radiation penetrated through the subject 2 is detected by the X-ray detection unit 3. Thereafter it is converted into analogue electrical signals, and the analogue electrical signals are converted into digital electrical signals. These signals are applied to the image processing unit 4 through the image data bus DB1.

Figure 7A:
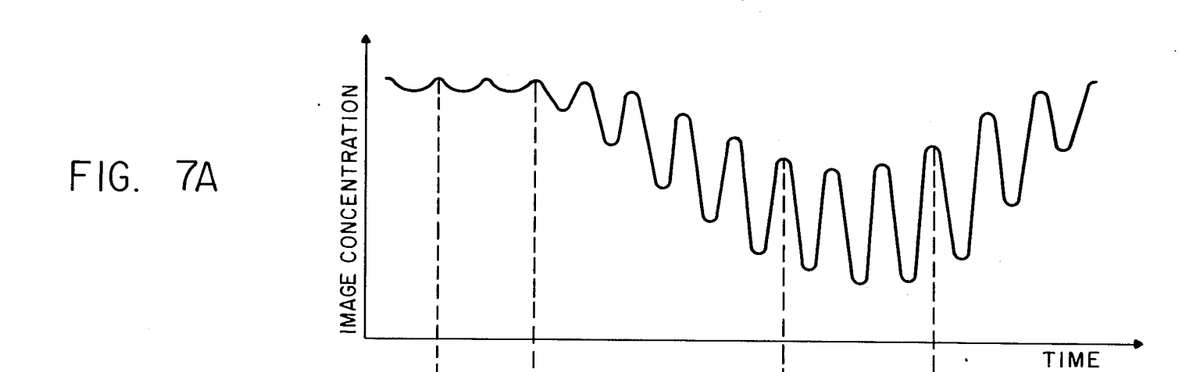
FIG. 7 is a timing diagram explaining operation of the preferred embodiment of the invention; and, FIG. 8 is a block diagram of an internal circuit of the timing controller in conjunction with the cardiograph unit.
Figure 7B:
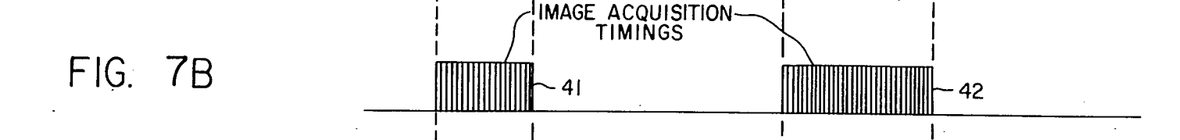
Figure 7C:
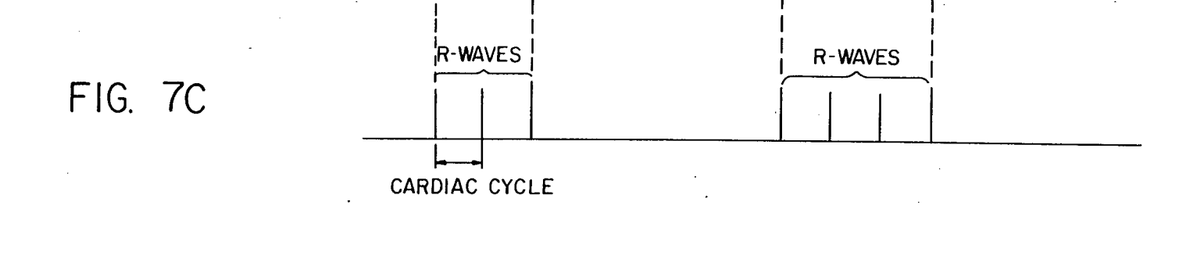

The image data obtained in the above-mentioned operation are first applied to the image concentration device 121 and are stored in the predetermined address area in the image storage section 25 through the image data bus DB2 in the order obtained. Thereafter, the averaged concentrations in the ROI are measured. Furthermore, the image data are applied to the image display unit 5 via the image data bus DB3 for display, to the selector 26 and to the image data bus DB5. FIGS. 7A-7C illustrate the above operation.

FIG. 7A shows the time-elapse characteristic curve of the image concentrations in the ROI. In FIG. 7A, the cardiac beat and the change in the contrast medium concentration are displayed. Image acquisition timings for projecting the X-ray are indicated by reference numerals 41 and 42 in FIG. 7B. At the image acquisition timing 41, the images are acquired before the injection of the contrast medium for two cardiac cycles, and at the image acquisition timing 42, the images are obtained after the injection of the contrast medium for three cardiac cycles. R waves of the cardiac beat are shown in FIG. 7C.

After the X-ray irradiation, the averaged concentrations are sequentially stored in one frame memory of the image storage section 25 and are also applied to the image display unit 5 for display thereby. Simultaneously, these concentrations are applied to the device 22 via the image data bus DB3 or DB4.

In this device 22, the cardiac beat phase numbers are corresponded to the cardiac image numbers, and these corresponded numbers are applied to the image processing controller 20 under control of a control signal line U.

The image processing controller 20 applies the weighting coefficients G1 and G2 to the background removing device 23 under control of a control signal P3 in accordance with the pulsatory cardiac movement information supplied from the device 22 and the averaged concentrations supplied from the image storage section 25, the cardiac image numbers of the mask images MI(i) and the contrast image CI(i) synchronized with each cardiac phase are sequentially supplied to the background removing device 23 through the image data buses DB3 and DB4.

The background removing device 23 which performs the image processing operation between the mask and contrast images (MI(i), and CI(i)) synchronized with each cardiac phase then processes the substracted images (SI(i)) and removes the background which does not contain the injected contrast mediums as shown in FIG. 3.

In other words, the mask images MI(i) and the contrast images CI(i) in one phase timing (i) are calculated and $SI(i) = MI(i) - CI(i)$ determined by the background removing device 23 as to K frame images in one cardiac beat. The weighting coefficients G1 and G2 are set to 1 and −1, and the subtracted images SI(i) obtained by the above calculation are stored in the image storage section 25 via the image data bus DB2.

The substracted images SI(i) stored in the storage section 25 are simultaneously supplied to the image display unit 5 through either of the image data buses DB3 or DB4 and the selector 26 for display by the image display unit 5.

Next, the process for calculating the amplitude and the phase images AI and PI from the the subtracted images SI(i) in one cardiac beat is illustrated in FIGS. 5 and 6.

Assuming that the substracted images SI(i) have K frames in one cardiac beat and the cardiac beat period is represented as T·K, the time of K-the frame of subtracted image SI(k) is expressed as $t = (k-1)T$ when $(1 \leq k \leq K)$ where T indicates the image sampling time interval.

If the image pixel concentration value located in (x, y) coordinates is defined as PC (x, y, t), the time change of PC (x, y, t) is approximated by the following equation (2):

$$PC(x, y, t) = a0/2 + a1 \cos(2\pi t/KT) + b1 \sin(2\pi t/Kt) \quad (2)$$

The coefficient a1 and b1 included in the equation (2) can be calculated by following equations (3) and (4)

$$a1 = (2/K) \sum_{k=1}^{k} PC[x, y, (k-1)T] \cos[2\pi(k-1)/K] \quad (3)$$

$$b1 = (2/K) \sum_{k=1}^{k} PC[x, y, (k-1)T] \sin[2\pi(k-1)/K \quad (4)$$

Here, where $$A1 = \sqrt{a1^2 + b1^2}$$

and $P1 = \tan^{-1}(b1/a1)$, then the equation (2) can be converted to the following equation (5):

$$PC(x, y, t) = a0/2 + A1 \sin(2\pi t/KT + P1) \quad (5)$$

A1 and P1 respectively indicate values of amplitude and phase of PC(x, y, t).

Next the sequential operation for calculating the coefficients a1 and b1 is explained.

The data in one frame memory of the image storage section 25 is cleared to zero. The zero cleared data SI(0) are supplied to the time filtering device 242 in the device 24 through the image data bus DB3. The first subtracted image data SI(1) is also supplied to the time filtering device 242. The device 242 multiplies the zero-cleared data SI(0) by the weighting coefficient F0 and the first image data SI(1) by the coefficient F1. The two multiplied image data are added, and thereafter the added image data are stored in the image storage section 25 through the data bus DB2.

At the next step, the device 242 reads the added data and the second subtracted image data SI(2) from the section 25, multiplies the same by F0 and F2, respectively, and stores the sum of the multiplied data in section 25. This operation is repeated until k becomes K. In this operation a1 image data a1(x, y) are produced. Now assuming that image data SI(0) are all 0 and F0 is 1. The a1 image data a1(x, y) are represented as follows, $$a1(x, y) = \sum_{k=1}^{k} Fk \cdot SI(k),$$

where $Fk = (2/K) \cdot \cos(2t(k-1)/K)$, and $SI(k) = PC[x, y, (k-1)T]$.

A similar operation is performed to obtain b1 image data. The difference between a1 image data and b1 image data is that for b1 image data Fk is defined as follows, $$Fk = (2/K) \sin(2t(k-1)/K).$$

Therefore, b1 image data, b1(x, y), are represented as follows, $$b1(x,y) = (2/K) \sum_{k=1}^{k} \sin(2t(k-1)/K) \cdot PC[x,y,(k-1)T].$$

These image data a1(x, y) and b1(x, y) are stored in the section 25.

Next, the calculated a1 image data a1(x, y) stored in the image storage section 25 are supplied to the amplitude imaging device 11 through the data bus DB3, and the calculated b1 image data b1(x, y) stored in the image storage section 25 are also supplied to the amplitude imaging device 11. The device 11 determines the square root of the sum of the square of the two image data to obtain amplitude image AI(x, y)

$$( = \sqrt{a1(x,y)^2 + b1(x,y)^2} ).$$

The calculated image AI(x, y) is stored in the image storage section 25 via the data bus DB2.

Similarly, the a1 image data a1(x, y) and the b1 image data b1(x, y) are supplied to the phase imaging device 12 to obtain a phase image $PI(x, y)(=tan^{-1}(b1(x, y)/a1(x, y)))$. The calculated image PI(x, y) is stored in a frame memory different from the frame memory of the image AI(x, y) in the image storage section 25.

The amplitude image AI(x, y) and phase image PI(x, y) are supplied to the selector 26 via the image data buses DB3 and DB4 for display thereof.

In these images AI(x, y) and PI(x, y) abnormal portions of amplitude and/or phase of the cardiac beat movement in the ROI are indicated brighter than the normal portions. Further, the abnormal portions may be indicated in different color from the normal portions, by a device for converting images into colored areas.

As the above specific embodiment of the present invention has been described, since the amplitude image and the phase image can be obtained by using one cardiac beat of X-ray cardiac penetrating image, and these images can be displayed with high speed, the cardiac function can be measured and evaluated quantitatively. Moreover, since the background of the X-ray penetrating images are removed by way of a subtracting operation between the mask images and the contrast images synchronized with the cardiac phase of the subject, the artifact according to the difference of the cardiac beat movement is less. Furthermore, the accuracy of the amplitude and phase images are high enough to enable diagnosis of the condition of the heart.

The present invention is not limited to the embodiment above described and shown in the accompanying drawings, but various changes and modifications may be made within the spirit and scope of the present invention.

For example, in the above embodiment, time-change data of image concentration are obtained to define the cardiac beat period. However, a cardiograph unit can be used to obtain a period of cardiac beat. As indicated by the broken line FIG. 1, the cardiograph unit 10 is connected to the timing controller 6.

Figure 8:
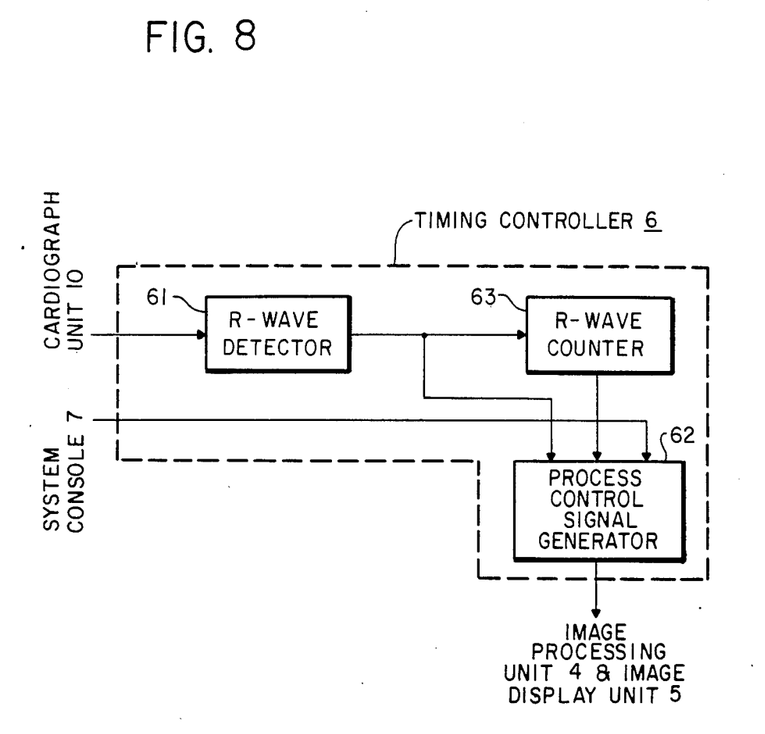

FIG. 8 shows an internal circuit of the timing controller 6. In FIG. 8, an output signal (i.e., cardiac beat signal) from a cardiograph unit 10 is supplied to an R wave detector 61. Thus, an R-wave component in a cardic cycle is detected. The R-wave component is supplied to process control signal generator 62 which generates control signals. These control signals are mainly supplied to an image processing unit 4. In this way, the detector 22 in the image processing unit 4 may be omitted.

Also, a linear Fourier function conversion was used to obtain the amplitude and the phase images. However, the amplitude and the phase images can be obtained using a high-degree Fourier function conversion in which the weighting coefficients Fk are changed to high degree sine and cosine functions in the device for biological functions.

Furthermore, in the above described embodiment, the image processing unit was formed of the device for producing time-elapse characteristic data of image concentration, the device for detecting cardiac beat period, the background removing device and the device for measuring biologic functions. However, the function of the image processing unit in obtaining the amplitude and phase images can be performed directly by the biological function measuring device in the period of one cardiac beat. However, in this case diagnosis efficiency is somewhat inferior to the above embodiment.

Obviously, numerous additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An apparatus for examining a subject by applying radiation to said subject in synchronism with a cardiac beat phase thereof, comprising:
   means for generating radiation;
   means for controlling the radiation generating means so as to project the radiation toward the subject at a predetermined time period;
   means for detecting the radiation which has been transmitted through the subject and for producing successively radiation transmission images thereof as digital image signals;
   means for temporarily storing a plurality of digital image signals that have been acquired at least during one cardiac beat period respectively before and after a radiation contrast medium arrives in a region of interest within the subject;
   means for detecting the cardiac beat period of the subject;
   means for quantitatively measuring the biological function of the subject based on the digital image signals acquired at least during one cardiac beat period before and after the penetration of radiation contrast medium into the subject including a time-filtering processor for repeatedly multiplying said digital image signals by respective weighting coefficients and adding said subsequent multiplied signals successively over the one whole cardiac period in synchronism with a given cardiac beat phase to produce time-filtered image signals; and
   means for displaying the biological function of the subject based on said time-filtered image signals.

2. An apparatus as claimed in claim 1, wherein said means for detecting the cardiac beat period of the subject comprises:
   means for producing data on time-elapse characteristics of image concentration from each of the digital image signals acquired at least during one cardiac beat period before and after the radiation contrast medium arrives in said region of interest; and
   means for detecting the cardiac beat period from said data on time-elapse characteristics of image concentration.

3. An apparatus as claimed in claim 1, wherein said means for detecting the cardiac beat period of the subject comprises a cardiograph unit.

4. An apparatus as claimed in claim 3, further comprising:
   an R-wave detector for detecting R-waves of cardiac beat derived from the cardiograph unit; and an R-wave counter for counting detected R-waves of cardiac beats.

5. An apparatus as claimed in claim 1, wherein said biological function measuring means comprises:
means for calculating amplitude image data and phase image data based on said time-filtered image signals so as to enable quantitative diagnosis of the subject.

6. An apparatus as claimed in claim 5, wherein said biological function measuring means comprises:
first and second multipliers for multiplying by first and second filter weighting coefficients the digital image signals acquired at least during one cardiac beat period before and after arrival of the radiation contrast medium in a region of interest in said subject; and
an adder for adding the image signals multiplied by said first weighting coefficient to the image signals multiplied by said second weighting coefficient so as to obtain background removed digital image signals applied to said time-filtering processor.

7. An apparatus as claimed in claim 5, wherein said time-filtering processor produces first image data and second image data, and wherein said amplitude image calculation means comprises:
means for squaring the first image data and the second image data obtained by said time-filtering processor;
adder means for adding the squared first image data and the squared second image data;
a square root calculation device for calculating the square root of the sum of the squared first image data and the squared second image data; and
gray-level converter means for converting said square root to gray-level amplitude image data having density information.

8. An apparatus as claimed in claim 5, wherein said time-filtering processor produces first image signals and second image signals, and wherein said calculating means comprises:
a reciprocal device for obtaining the reciprocal of the first image data;
a multiplier for multiplying said reciprocal of the first image data by the second image data to obtain the product thereof;
arc-tangent calculation means for determining the arc-tangent of said product; and
gray-level converter means for converting the calculated arc-tangent to gray-level phase image data having density information.

9. An apparatus as claimed in claim 1, further comprising:
means for removing background image data between the digital image signals respectively acquired at least during one cardiac beat period before and after arrival of a radiation contrast medium in a region of interest in the subject.

10. An apparatus for examining a subject by applying radiation to said subject in synchronism with a cardiac beat phase thereof, comprising:
means for generating radiation;
means for controlling the radiation means so as to project the radiation toward the subject at a predetermined time period;
means for detecting the radiation which has been transmitted through the subject and for producing successively radiation transmission images thereof as digital image signals;
means for temporarily storing a plurality of digital image signals that have been acquired at least during two cardiac beat periods of the subject;
means for detecting the cardiac beat period of the subject;
means for measuring a biological function based on the digital image signals acquired at least during two cardiac beat periods, including a time-filtering processor for repeatedly multiplying said digital image signals by respective weighting coefficients and adding said subsequent multiplied signals successively over the one whole cardiac period in synchronism with a given cardiac beat in each of the two different cardiac beat periods so as to obtain time-filtered digital image signals; and
means for diplaying the biological function based on the time-filtered digital image signals.

11. An apparatus as claimed in claim 10, wherein said means for detecting the cardiac beat period of the biological unit comprises a cardiograph unit.

12. An apparatus as claimed in claim 11, further comprising:
an R-wave detector for detecting R-waves of cardiac beats derived from the cardiograph unit; and
an R-wave counter for counting detected R-waves of cardiac beats.

13. An apparatus as claimed in claim 10, wherein said biological function measuring means comprises:
means for calculating amplitude image data and phase image data so as to enable quantitative diagnosis of the subject based on the time-filtered digital image signals.

14. An apparatus as claimed in claim 13, wherein said biological function measuring means comprises:
first and second multipliers for multiplying by first and second filter weighting coefficients the digital image signals acquired at least during two cardiac beat periods prior to a given cardiac beat period; and
an adder for adding the imge signals multiplied by the first weighting coefficient to the image signals multiplied by the second weighting coefficient so as to obtain a background removed digital signals applied to said time-filtering processor.

15. An apparatus as claimed in claim 13, wherein said time-filtering processor produces first image data and second image data, and wherein said calculating means comprises:
means for squaring the first image data and the second image data;
an adder for adding the squared first image data and the squared second image data;
a square root calculation device for calculating the square root of the sum of the squared first image data and the squared second image data; and
gray-level converter means for converting said square root to gray-level amplitude image data having density information.

16. An apparatus as claimed in claim 13, wherein said time-filtering processor produces first image data and second image data, and wherein said calculating means comprises:
a reciprocal device for obtaining the reciprocal of the first image data;
a multiplier for multiplying said reciprocal of the first image data by said second image data to obtain the product therof;

arc-tangent calculation device for determining the arc-tangent of said product; and gray-level converter means for converting the determined arc-tangent to gray-level phase image data having density information.

17. A method for measuring biological function of a region of a subject, comprising:

obtaining a plurality of mask image signals in a complete cardiac period before an X-ray contrast medium arrives in the region of the object;

obtaining a plurality of contrast image signals in another complete cardiac period after the X-ray contrast medium arrives in said region;

producing background removed image signals substantially affected by the contrast medium by subtracting the mask image signals from the contrast image signals in synchronization with the cardiac phase;

approximating a time-change of the background removed image signals into at least a first Fourier component image signal of a Fourier series representation thereof, wherein the Fourier series of background removed image signals $PC((x, y, t)$ is defined as follows:

$$PC(x, y, t) = Ao/2 + a1 \cos(2\pi t/Kt) + b1 \sin(2\pi t/Kt)T$$

and the first Fourier component is given by:

$$a1 \cos(2\pi t/Kt) + b1 \sin(2\pi t/Kt),$$

where a1 and b1 are coefficients and K is the number of data frames in the cardiac periods, comprising producing said a1 and b1 coefficients by repeatedly multiplying the background removed image signals by respective weighting coefficients and adding the subsequently multiplied signals over the whole cardiac period in synchronism with a given cardiac beat phase; and calculating at least one image of amplitude and phase of the first Fourier component image signal.

* * * * *